United States Patent
Lee et al.

(10) Patent No.: US 10,036,722 B2
(45) Date of Patent: Jul. 31, 2018

(54) ION CONCENTRATION MEASURING METHOD AND APPARATUS

(71) Applicant: KOREA INSTITUTE OF MACHINERY & MATERIALS, Daejeon (KR)

(72) Inventors: Kang-Ho Lee, Daejeon (KR); Oh Won Kwon, Daejeon (KR); Bong Seop Kwak, Daejeon (KR); Dong Kyu Lee, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 159 days.

(21) Appl. No.: 14/959,001

(22) Filed: Dec. 4, 2015

(65) Prior Publication Data
US 2016/0341690 A1 Nov. 24, 2016

(30) Foreign Application Priority Data

May 21, 2015 (KR) .................. 10-2015-0071087

(51) Int. Cl.
*G01N 27/00* (2006.01)
*G01N 27/414* (2006.01)

(52) U.S. Cl.
CPC .................. *G01N 27/4145* (2013.01)

(58) Field of Classification Search
CPC .............. G01R 25/00; G01R 31/31725; G01R 31/31922
USPC .................. 324/76.77, 76.11, 76.39
See application file for complete search history.

(56) References Cited

U.S. PATENT DOCUMENTS

| | | | | |
|---|---|---|---|---|
| 3,674,934 A | * | 7/1972 | Gooding | H04L 27/2275 375/336 |
| 4,414,675 A | * | 11/1983 | Comroe | H04L 27/2337 327/3 |
| 4,669,095 A | * | 5/1987 | Hall | H04L 27/2337 329/300 |
| 7,686,929 B2 | | 3/2010 | Toumazou | |
| 7,888,015 B2 | | 2/2011 | Toumazou | |
| 8,114,591 B2 | | 2/2012 | Toumazou | |
| 8,323,468 B2 | | 12/2012 | Kamahori | |

(Continued)

FOREIGN PATENT DOCUMENTS

| | | |
|---|---|---|
| JP | 2011-099877 | 5/2011 |
| JP | 2012-047761 | 3/2012 |
| JP | 2014-115125 | 6/2014 |

OTHER PUBLICATIONS

Toumazou, C., et al. "Simultaneous DNA amplification and detection using a pH-sensing semiconductor system", Nature Methods 10, pp. 641-646, Jun. 9, 2013.

(Continued)

*Primary Examiner* — Giovanni Astacio-Oquendo
(74) *Attorney, Agent, or Firm* — Lex IP Meister, PLLC

(57) ABSTRACT

An ion concentration measuring method and apparatus are provided. The ion concentration measuring apparatus includes an ion sensing layer in contact with a solution, a plurality of transistors having gate electrodes connected to the ion sensing layer, and a reading unit configured to change frequency information by using drain currents from the plurality of transistors and generate ion concentration information by using the frequency information.

14 Claims, 4 Drawing Sheets

(56) References Cited

U.S. PATENT DOCUMENTS

| | | | |
|---|---|---|---|
| 2008/0265985 A1 | 10/2008 | Toumazou | |
| 2010/0117666 A1* | 5/2010 | Wada | G01N 27/447 |
| | | | 324/705 |
| 2011/0025338 A1* | 2/2011 | Willey | G01N 27/42 |
| | | | 324/439 |
| 2012/0025853 A1* | 2/2012 | Chiu | H01L 22/10 |
| | | | 324/693 |

OTHER PUBLICATIONS

David Welch et al., "Real-time feedback control of pH within microfluidics using integrated sensing and actuation" Lab on a Chip, Issue 6, Jan. 23, 2014, 14, pp. 1191-1197.
W. S. Wan Zain, et al., "A Bulk-Driven ISFET-Based Chemical Mixer", IEEE, pp. 134-137, Nov. 5, 2010.

* cited by examiner

ION CONCENTRATION MEASURING METHOD AND APPARATUS

CROSS-REFERENCE TO RELATED APPLICATION

This application claims priority to and the benefit of Korean Patent Application No. 10-2015-0071087 filed in the Korean Intellectual Property Office on May 21, 2015, the entire contents of which are incorporated herein by reference.

BACKGROUND OF THE INVENTION (a) Field of the Invention

The present invention relates to an ion concentration measuring method and apparatus for electrically measuring a concentration of ions present in a liquid solution.

(b) Description of the Related Art

An ion concentration measuring apparatus measures a membrane potential generated in an ion sensing layer in contact with a solution and displays the measured membrane potential, and recently, application of the ion concentration measuring apparatus has extended to biosensors and gas sensors. For example, a typical ion concentration measuring apparatus detects hydrogen ions and displays a degree of pH.

The ion concentration measuring apparatus may detect an ion concentration using a semiconductor transistor according to a semiconductor detection method. In the related art semiconductor detection method, an ion sensitive field effect transistor (ISFET) is used. The ISFET refers to an FET in which an ion sensing layer replacing a metal electrode is provided at a gate part of a metal oxide semiconductor field effect transistor (MOSFET), in order to have ion selectivity. Using FET characteristics reacting to a potential on the ion sensing layer (that is, an interface potential), an ion concentration may be measured by indirectly measuring the interface potential. The semiconductor detection method is advantageous in that a response time is fast, allows the ion concentration detection apparatus to become compact and integrated, and allows for mass production.

In the related art ion concentration measuring apparatus using the ISFET, a single transistor including an ion sensing layer is used and an interface potential is induced as a voltage or a current at a source or a drain region of the ISFET, whereby the interface potential is indirectly measured. In the related art method, however, loss occurs in the process of inducing the interface potential as a voltage or a current at a source or a drain region, making it difficult to measure a fine interface potential (a potential on the ion sensing layer). Also, in the related art, since the single transistor including the single ion sensing layer is used, a measurement magnitude with respect to a membrane potential is limited to single transistor characteristics. With the method for measuring an ion concentration using a semiconductor, shielding (passivation) a solution such that it does not affect operation of a transistor or a circuit unit is important. However, in the related art ISFET, since the ion sensing layer and the transistor are positioned to be close up and down, a shielding process is difficult to perform and stability is degraded.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide an ion concentration measuring method and apparatus having advantages of measuring a fine interface potential.

The present invention has also been made in an effort to provide an ion concentration measuring method and apparatus having advantages of increasing stability.

An exemplary embodiment of the present invention provides an ion concentration measuring apparatus for measuring an ion concentration of a solution. The ion concentration measuring apparatus may include: an ion sensing layer in contact with the solution; a plurality of transistors having gate electrodes connected to the ion sensing layer; and a reading unit configured to receive drain currents from the plurality of transistors, change the drain currents into frequency information, and generate information regarding the ion concentration by using the frequency information.

The gate electrodes of the plurality of transistors may each be connected to the ion sensing layer through a gate metal, and at least a portion of a region of the gate metal excluding regions thereof in contact with the gate electrodes may be in contact with the ion sensing layer.

The reading unit may include: a ring oscillator configured to receive each of the drain currents and generate a square wave signal; a frequency divider configured to change a high frequency of the square wave signal into a lower frequency; and a counter configured to count pulses with respect to the square wave voltage of which frequency has been changed into the lower frequency, and generate the ion concentration information.

The ring oscillator may include a plurality of inverters configured to respectively receive the drain currents by bias terminals thereof, and output terminals and input terminals of the plurality of inverters may be connected to each other.

The plurality of transistors may be metal oxide semiconductor field effect transistors (MOSFETs).

Another exemplary embodiment of the present invention provides an ion concentration measuring method for measuring an ion concentration by using an ion sensing layer in contact with a solution. The ion concentration measuring method may include: converting an interface potential of the ion sensing layer into a plurality of currents by using a plurality of transistors having gate electrodes connected to the ion sensing layer; converting the plurality of currents into frequency information; and counting the frequency information to generate information regarding the ion concentration.

The converting into the frequency information may include: changing the plurality of currents into a square wave signal; and changing a frequency of the square wave signal into a lower frequency.

The plurality of currents may be drain currents of the plurality of transistors.

The gate electrodes of the plurality of transistors may each be connected to the ion sensing layer through a gate metal, and at least a portion of a region of the gate metal excluding regions thereof in contact with the gate electrodes may be in contact with the ion sensing layer.

Yet another exemplary embodiment of the present invention provides an ion concentration measuring apparatus. The ion concentration measuring apparatus may include: a first transistor having a gate electrode connected to an ion sensing layer; a second transistor having a gate electrode connected to the ion sensing layer; a first inverter configured to receive a drain current from the first transistor through a bias terminal thereof; a second inverter configured to receive a drain current from the second transistor through a bias terminal thereof, and having an input terminal connected to an output terminal of the first inverter; a third inverter having an input terminal connected to an output terminal of the second inverter and an output terminal connected to an input terminal of the first inverter; and a counter configured to count frequency information regarding pulses output from the output terminal of the third inverter.

The gate electrode of the first transistor and the gate electrode of the second transistor may be connected to the ion sensing layer through a gate metal, and at least a portion of a region of the gate metal, excluding regions thereof in contact with the gate electrode of the first transistor and the gate electrode of the second transistor, may be in contact with the ion sensing layer.

The ion concentration measuring apparatus may further include a frequency divider configured to receive the pulses from the output terminal of the third inverter and change a frequency of the pulses into a lower frequency to generate the frequency information.

The frequency information is changed according to the drain current of the first transistor and the drain current of the second transistor.

The ion concentration measuring apparatus may further include a third transistor having a gate electrode connected to the ion sensing layer, wherein a bias terminal of the third inverter receives a drain current from the third transistor.

According to an exemplary embodiment of the present invention, since a plurality of transistors are used, sensitivity may be enhanced.

In addition, according to an exemplary embodiment of the present invention, since the gate electrodes of the plurality of transistors are connected to the ion sensing layer through the extended gate metal, the ion sensing layer and the transistor are not positioned to be close up and down unlike the prior art. Therefore, a shielding process is easy to perform resulting an improvement in stability.

DETAILED DESCRIPTION OF THE EMBODIMENTS

Figure 1:
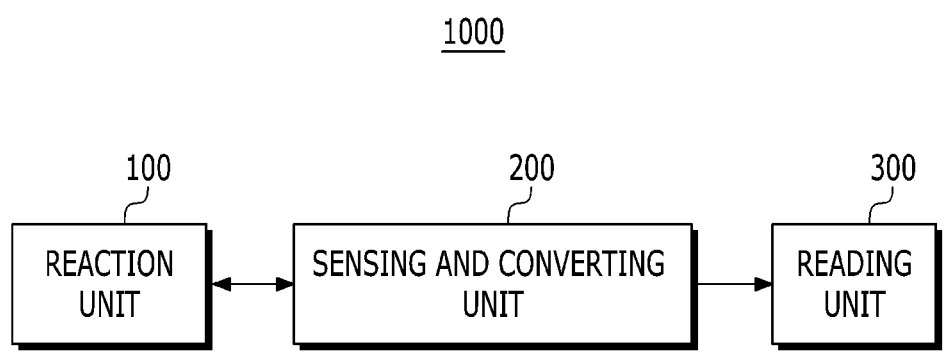
FIG. 1 is a block diagram schematically illustrating an ion concentration measuring apparatus according to an exemplary embodiment of the present invention.

Hereinafter, exemplary embodiments of the present invention will be described in detail with reference to the accompanying drawings, in which like numbers refer to like elements throughout and redundant descriptions thereof will be omitted. In the following description, usage of suffixes such as 'module', 'part', or 'unit' used for referring to elements is given merely to facilitate explanation of the present invention, without having any significant meaning by themselves. In describing the present invention, if a detailed explanation for a related known function or construction is considered to unnecessarily divert the gist of the present invention, such explanation has been omitted but would be understood by those skilled in the art. The accompanying drawings of the present invention aim to facilitate understanding of the present invention and should not be construed as limited to the accompanying drawings. Also, the present invention is not limited to a specific disclosed form, but includes all modifications, equivalents, and substitutions without departing from the scope and spirit of the present invention.

It will be understood that, although the terms first, second, etc. may be used herein to describe various elements, these elements should not be limited by these terms. These terms are only used to distinguish one element from another.

It is to be understood that when one element is referred to as being "connected to" or "coupled to" another element, it may be connected or coupled directly to the other element or be connected or coupled to the other element having another element intervening therebetween. On the other hand, it is to be understood that when one element is referred to as being "connected directly to" or "coupled directly to" another element, it may be connected or coupled to the other element without another element intervening therebetween.

As used herein, the singular forms "a", "an", and "the" are intended to include the plural forms as well, unless the context clearly indicates otherwise.

In the drawings, the thicknesses of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Hereinafter, exemplary embodiments of the present invention will be described in detail to be easily embodied by those skilled in the art with reference to the accompanying drawings. The present invention may, however, be embodied in many different forms and should not be construed as being limited to the embodiments set forth herein.

An ion concentration measuring method and apparatus according to an exemplary embodiment of the present invention use a plurality of transistors in order to measure an ion concentration, and gate electrodes of the plurality of transistors extend to be connected to an ion sensing layer. In the ion concentration measuring method and apparatus according to an exemplary embodiment of the present invention, in order to use characteristics of the plurality of transistors, a membrane potential is converted into a plurality of independent currents and an ion concentration is read through a ring oscillator. Hereinafter, the ion concentration measuring method and apparatus according to an exemplary embodiment of the present invention will be described in detail with reference to FIGS. 1 through 3.

Figure 2:
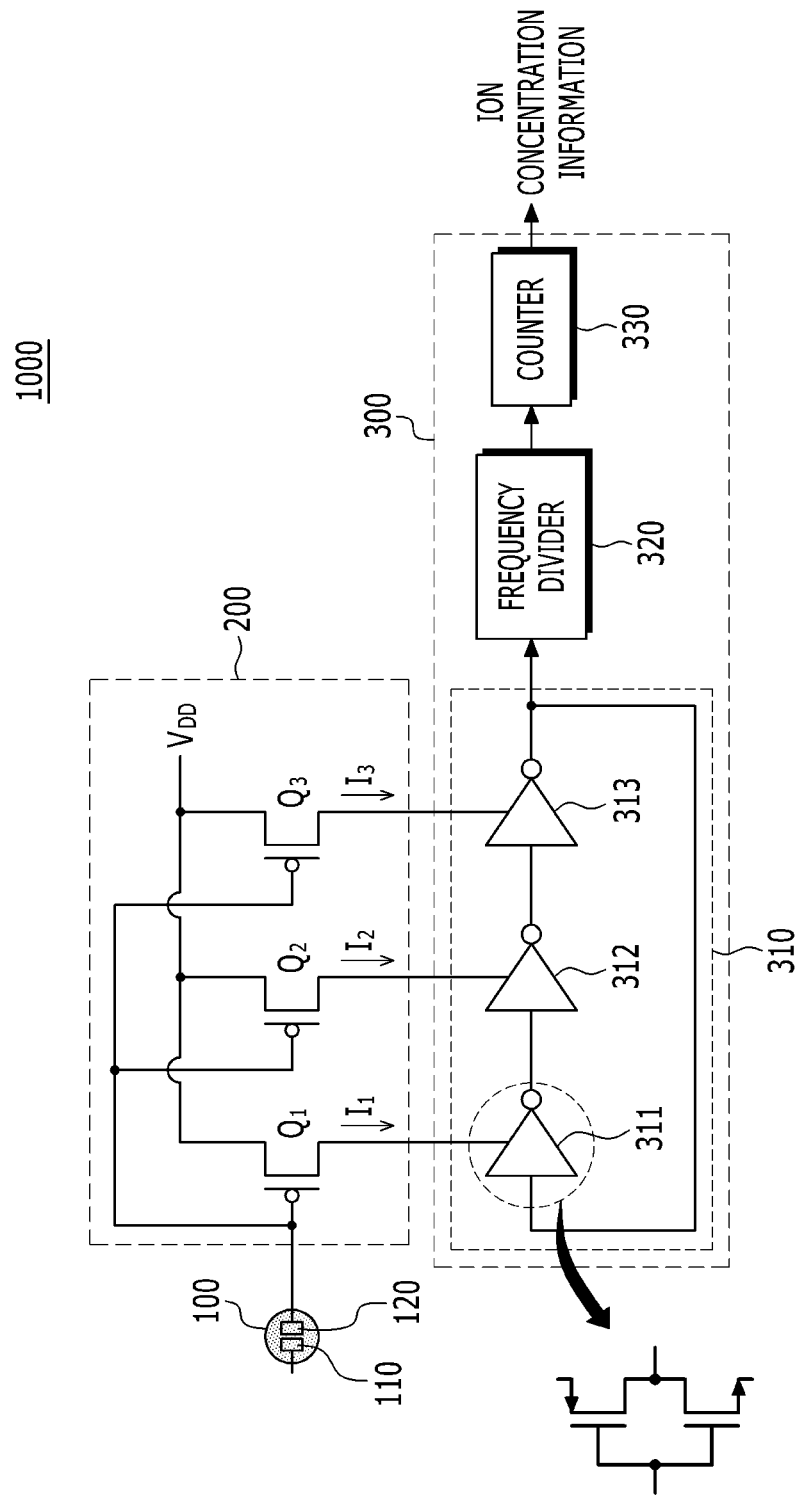
FIG. 2 is a circuit diagram specifically illustrating the ion concentration measuring apparatus according to an exemplary embodiment of the present invention.

FIG. 1 is a block diagram schematically illustrating an ion concentration measuring apparatus according to an exemplary embodiment of the present invention, and FIG. 2 is a circuit diagram specifically illustrating the ion concentration measuring apparatus according to an exemplary embodiment of the present invention.

As illustrated in FIG. 1, an ion concentration measuring apparatus 1000 according to an exemplary embodiment of the present invention includes a reaction unit 100, a sensing and converting unit 200, and a reading unit 300.

Referring to FIG. 2, the reaction unit 100 includes a reference electrode 110 and an ion sensing layer 120. The reference electrode 110 and the ion sensing layer 120 come into contact with a solution of which ion concentration is to be measured. A predetermined reference voltage Vref is applied to the reference electrode 110, and a potential of the ion sensing layer 120 (that is, an interface potential) is varied according to ion concentrations of a solution. As described with reference to FIG. 3 hereinafter, the ion sensing layer 120 according to an exemplary embodiment of the present invention is connected to a gate metal 220 extending gate electrodes 210-1 to 210-3. A specific material and reaction characteristics of the ion sensing layer 120 may be known by a person skilled in the art to which the present invention pertains, and thus a detailed description thereof will be omitted.

The sensing and converting unit 200 senses an interface potential (a potential of the ion sensing layer 120) according to an ion concentration, and converts the sensed interface potential into a current. As illustrated in FIG. 2, the sensing and converting unit 200 according to an exemplary embodiment of the present invention includes a plurality of transistors. In FIG. 2, for the purpose of description, three transistors Q1 to Q3 are illustrated, and the number of transistors may be at least two. Also, in FIG. 2, the transistors Q1 to Q3 are illustrated as MOSFETs, but these transistors may be replaced with other FETs such as junction FETs (J-FETs).

A specific configuration of the sensing and converting unit 200 will be described in detail with reference to FIGS. 2 and 3.

Figure 3:
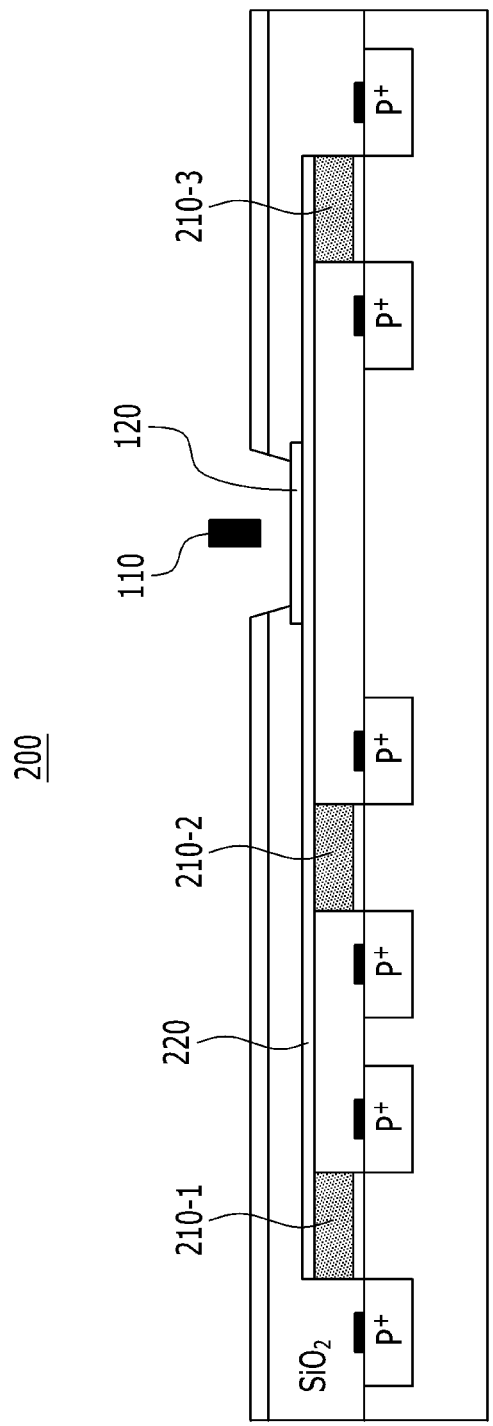
FIG. 3 is a cross-sectional view illustrating a sensing and converting unit according to an exemplary embodiment of the present invention.

FIG. 3 is a cross-sectional view illustrating the sensing and converting unit 200 according to an exemplary embodiment of the present invention. In FIG. 3, a plurality of transistors Q1 to Q3 are illustrated as P-type MOSFETs for the purpose of description, but these transistors Q1 to Q3 may be N-type MOSFETs.

As illustrated in FIG. 2, the sensing and converting unit 200 includes the plurality of transistors Q1 to Q3. Source regions of the plurality of transistors Q1 to Q3 are connected to a bias power source $V_{DD}$. Gate regions of the plurality of transistors Q1 to Q3 are connected to each other and connected to the ion sensing layer 120.

Referring to FIG. 3, the gate electrodes 201-1 to 210-3 of the plurality of transistors Q1 to Q3 according to an exemplary embodiment of the present invention are connected to the ion sensing layer 120 through the extended gate metal 220, rather than being directly connected to the ion sensing layer 120. That is, the gate metal 220 extends along upper surfaces of the gate electrodes 210-1 to 210-3 of the plurality of transistors Q1 to Q3, and at least a portion of a region of the gate metal 220 excluding regions thereof in contact with the gate electrodes 210-1 to 210-3 of the plurality of transistors Q1 to Q3 is in contact with the ion sensing layer 120. In this manner, since the gate electrodes 210-1 to 210-3 of the plurality of transistors Q1 to Q3 are connected to the ion sensing layer 120 through the gate metal 220, exposure of the plurality of transistors Q1 to Q3 and other circuit units (for example, 300) to a solution may be minimized. Thus, shielding (or passivation) is facilitated and only the reaction unit 100 including the ion sensing layer 120 may be manufactured to be disposable and easily used.

Meanwhile, drain currents I1, I2, and I3 of the plurality of transistors Q1 to Q3 are independently varied according to an interface potential and are input to the reading unit 300.

The reading unit 300 receives the drain currents I1, I2, and I3 converted by the plurality of transistors Q1 to Q3, and generates ion concentration information using the drain currents I1, I2, and I3. As illustrated in FIG. 2, the reading unit 300 according to an exemplary embodiment of the present invention includes a ring oscillator 310, a frequency divider 320, and a counter 330.

Figure 4:
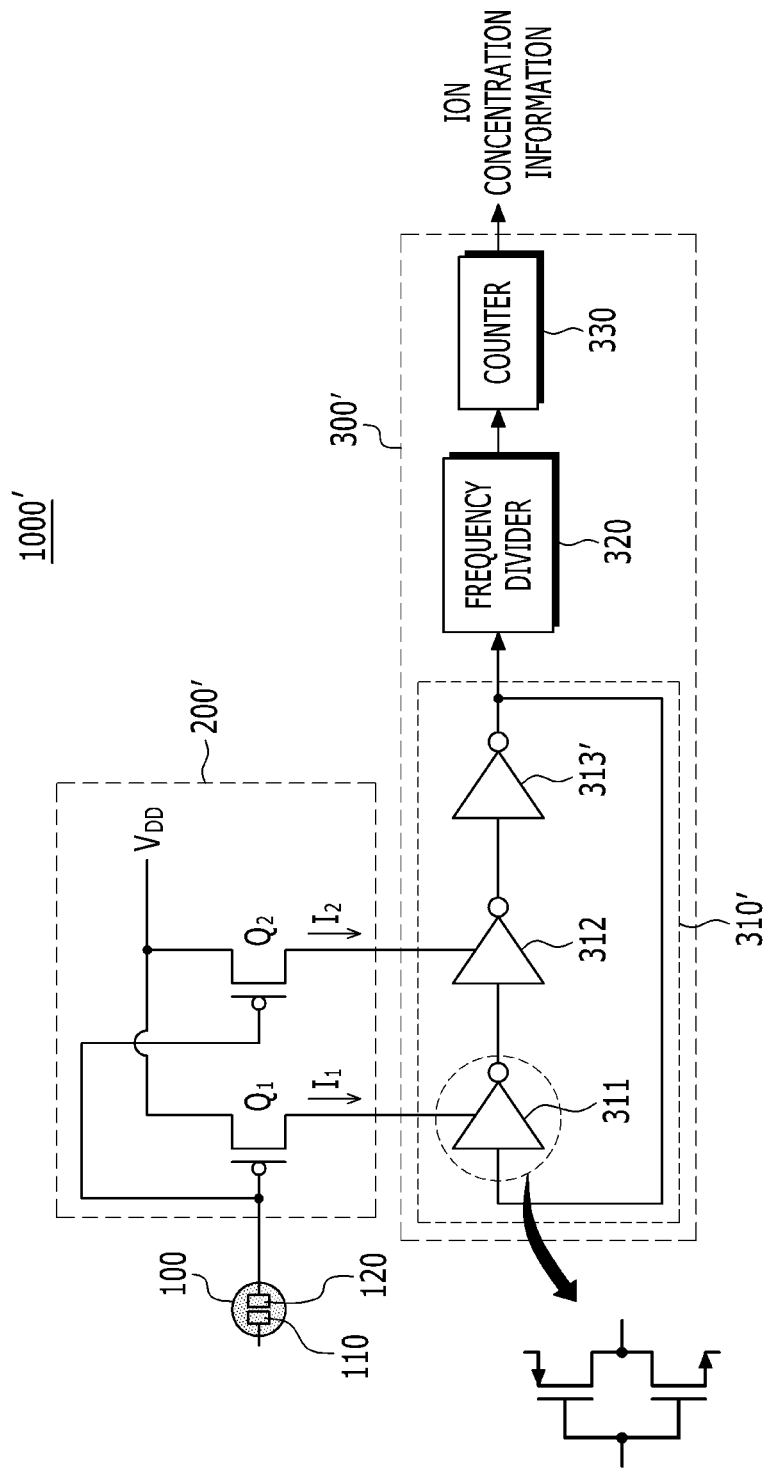
FIG. 4 is a circuit diagram illustrating an ion concentration measuring apparatus according to another exemplary embodiment of the present invention.

The ring oscillator 310 includes a plurality of inverters 311 to 313. The ring oscillator 310 receives the drain currents I1, I2, and I3, and generates a square wave signal having a frequency that is changed according to magnitudes of the drain currents I1, I2, and I3. In FIG. 2, three inverters are illustrated, but the number of the inverters may be changed in condition that oscillating activity is allowed. That is, as illustrated in FIG. 4, the number of inverters may be equal to or greater than the number of transistors. The plurality of inverters 311 to 313 have a structure in which a P-type FET and an N-type FET are connected in series, serving to invert an input level.

The plurality of inverters 311 to 313 each includes an input terminal, an output terminal, and a bias terminal. The input terminal is a terminal to which an input level is input, and the output terminal is a terminal from which an inverted input level is output. The bias terminal is a terminal to which bias power is input, which corresponds to a source terminal of a P-type FET. The plurality of inverters 311 to 313 according to an exemplary embodiment of the present invention receive the drain currents I1, I2, and I3, respectively, through the bias terminal thereof. That is, the bias terminal of the inverter 311 is connected to the drain region of the transistor Q1, the bias terminal of the inverter 312 is connected to the drain region of the transistor Q2, and the bias terminal of the inverter 313 is connected to the drain region of the transistor Q3. The output terminal of the inverter 311 is connected to the input terminal of the inverter 312, the output terminal of the inverter 312 is connected to the input terminal of the inverter 313, and the output terminal of the inverter 313 is connected to the input terminal of the inverter 311. In this manner, the plurality of inverters 311 to 313 are connected in an annular form to be oscillated, and generate a square wave signal. The square wave signal generated by the ring oscillator 310 is changed in frequency according to the drain currents I1, I2, and I3.

The frequency divider 320 receives the square wave signal from the ring oscillator 310, and changes a high frequency of the square wave signal into a low frequency. A method of changing a frequency by the frequency divider 320 is known to a person skilled in the art to which the present invention pertains, and thus a detailed description thereof will be omitted.

The counter 320 counts the number of pulses of the square wave signal having a frequency that is changed to be lower by the frequency divider 320. A final value output by the counter 320 corresponds to ion concentration information (that is, information regarding an interface potential). A method of counting the number of pulses by the counter 320 is known to a person skilled in the art to which the present invention pertains, and thus a detailed description thereof will be omitted.

Hereinafter, an overall operation of the ion concentration measuring apparatus according to an exemplary embodiment of the present invention will be described with reference to FIGS. 1 through 3.

The plurality of transistors Q1 to Q3 convert interface potentials of gate regions into mutually independent currents. Here, in a case in which the plurality of transistors Q1 to Q3 are implemented as FETs, the converted currents I1, I2, and I3 are expressed as a square of a gate potential term ($V_G$) as expressed by Equation 1 below.

$$I_D = k \frac{W}{L} \cdot (V_{GS} - V_T)^2 (1 + qV_{DS}) \quad \text{[Equation 1]}$$

In Equation 1, $I_D$ corresponds to the currents I1, I2, and I3. K is a Boltzmann constant, and q is a charge amount of electrons, that is, $1.6 \cdot 10^{-19}$ C. W and L are a width and a length of a transistor channel, respectively. $V_{GS}$ is a voltage across gate and source region of a transistor.

In a case in which the interface potential ($V_G$) is converted into the currents I1, I2, and I3, since the currents I1, I2, and I3 are reflected as a square, sensitivity is increased for a first time. The plurality of different currents I1, I2, and I3 are input to the ring oscillator 310, and converted into frequency information by the ring oscillator 310. Since the frequency information is affected by all of the plurality of different currents I1, I2, and I3, sensitivity is increased for a second time.

The ring oscillator 310 includes the plurality of inverters 311 to 313. A frequency of a square wave signal output from the ring oscillator 310 is changed according to amounts of currents (that is, I1, I2, and I3) flowing in the bias terminals of the inverters 311 to 313. The square wave voltage signal appears as a capacitor component present as an output terminal of an inverter is charged or discharged. That is, when the currents I1, I2, and I3 are large, the capacitor components of the output terminals of the inverters 311 to 313 may be quickly charged or discharged, and thus, the frequency of the square wave signal may be increased. Also, when the currents I1, I2, and I3 are small, the capacitor components of the inverters 311 to 313 are charged or discharged slowly, and thus the frequency of the square wave signal is decreased.

The frequency information (frequency of the square wave signal) as an output from the ring oscillator 310 is converted into a low frequency by the frequency divider 320. Finally, the counter 320 counts the frequency information to generate ion concentration information (that is, information regarding an interface potential).

FIG. 4 is a circuit diagram illustrating an ion concentration measuring apparatus 1000' according to another exemplary embodiment of the present invention.

As illustrated in FIG. 4, a sensing and converting unit 200' according to another exemplary embodiment of the present invention is the same as the sensing and converting unit 200 illustrated in FIG. 2, except that it includes two transistors Q1 and Q2 and a bias terminal of an inverter 313' is not connected to a transistor.

As described above, the number of inverters may be configured to be equal to or greater than the number of transistors, and in the case of FIG. 4, three inverters and two transistors are provided. An ion concentration measuring apparatus 1000' according to another exemplary embodiment of the present invention operates in the same manner as that of the ion concentration measuring apparatus 1000 of FIG. 2, except that two transistors are provided, and thus a detailed description thereof will be omitted.

According to the exemplary embodiment of the present invention, since the ion detection method based on a semiconductor is provided, it advantageously has a compact size and allows for integration and may be developed as a low-priced unit.

Also, according to an exemplary embodiment of the present invention, since the existing MOSFET is used as is, a commercial CMOS semiconductor process may be used as is. Thus, the manufacturing cost may be reduced. In the case of the related art ISFET, the gate metal electrode should be replaced with an ion sensing layer, requiring an additional process after the FET is manufactured.

According to an exemplary embodiment of the present invention, since the structure connected by using a plurality of transistors is provided and an interface potential is converted into a plurality of independent currents, sensitivity may be enhanced. Thus, a fine interface potential (that is, a membrane potential) may be detected.

Also, according to an exemplary embodiment of the present invention, since a plurality of independent currents are input to the ring oscillator and converted into frequency information and the frequency information is counted, analog information may be easily converted into a digital signal.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An ion concentration measuring apparatus for measuring an ion concentration of a solution, the ion concentration measuring apparatus comprising:
   an ion sensing layer in contact with the solution;
   a plurality of transistors having gate electrodes connected to the ion sensing layer; and
   a reading unit configured to receive drain currents from the plurality of transistors, change the drain currents into frequency information, and generate information regarding the ion concentration by using the frequency information.

2. The ion concentration measuring apparatus of claim 1, wherein
   the gate electrodes of the plurality of transistors are each connected to the ion sensing layer through a gate metal, and
   at least a portion of a region of the gate metal excluding regions thereof in contact with the gate electrodes is in contact with the ion sensing layer.

3. The ion concentration measuring apparatus of claim 1, wherein
   the reading unit includes:
   a ring oscillator configured to receive each of the drain currents and generate a square wave signal;
   a frequency divider configured to change a high frequency of the square wave signal into a lower frequency; and
   a counter configured to count pulses with respect to the square wave signal of which frequency has been changed into the lower frequency, and generate the ion concentration information.

4. The ion concentration measuring apparatus of claim 3, wherein
   the ring oscillator includes a plurality of inverters configured to respectively receive the drain currents by bias terminals thereof, and
   output terminals and input terminals of the plurality of inverters are connected to each other.

5. The ion concentration measuring apparatus of claim 1, wherein
   the plurality of transistors are metal oxide semiconductor field effect transistors (MOSFETs).

6. An ion concentration measuring method for measuring an ion concentration by using an ion sensing layer in contact with a solution, the ion concentration measuring method comprising:
    converting an interface potential of the ion sensing layer into a plurality of currents by using a plurality of transistors having gate electrodes connected to the ion sensing layer;
    converting the plurality of currents into frequency information; and
    counting the frequency information to generate information regarding the ion concentration.

7. The ion concentration measuring method of claim 6, wherein
    the converting into the frequency information includes:
    changing the plurality of currents into a square wave signal; and
    changing a frequency of the square wave signal into a lower frequency.

8. The ion concentration measuring method of claim 6, wherein
    the plurality of currents are drain currents of the plurality of transistors.

9. The ion concentration measuring method of claim 6, wherein
    the gate electrodes of the plurality of transistors each are connected to the ion sensing layer through a gate metal, and
    at least a portion of a region of the gate metal excluding regions thereof in contact with the gate electrodes is in contact with the ion sensing layer.

10. An ion concentration measuring apparatus comprising:
    a first transistor having a gate electrode connected to an ion sensing layer;
    a second transistor having a gate electrode connected to the ion sensing layer;
    a first inverter configured to receive a drain current from the first transistor through a bias terminal thereof;
    a second inverter configured to receive a drain current from the second transistor through a bias terminal thereof, and having an input terminal connected to an output terminal of the first inverter;
    a third inverter having an input terminal connected to an output terminal of the second inverter and an output terminal connected to an input terminal of the first inverter; and
    a counter configured to count frequency information regarding pulses output from the output terminal of the third inverter.

11. The ion concentration measuring apparatus of claim 10, wherein
    the gate electrode of the first transistor and the gate electrode of the second transistor are connected to the ion sensing layer through a gate metal, and
    at least a portion of a region of the gate metal, excluding regions thereof in contact with the gate electrode of the first transistor and the gate electrode of the second transistor, is in contact with the ion sensing layer.

12. The ion concentration measuring apparatus of claim 10, further comprising
    a frequency divider configured to receive the pulses from the output terminal of the third inverter and change a frequency of the pulses into a lower frequency to generate the frequency information.

13. The ion concentration measuring apparatus of claim 10, wherein
    the frequency information is changed according to the drain current of the first transistor and the drain current of the second transistor.

14. The ion concentration measuring apparatus of claim 10, further comprising
    a third transistor having a gate electrode connected to the ion sensing layer,
    wherein a bias terminal of the third inverter receives a drain current from the third transistor.

* * * * *